US006100274A

United States Patent [19]
Kou

[11] Patent Number: 6,100,274
[45] Date of Patent: *Aug. 8, 2000

[54] 8-CHLORO-6,11-DIHYDRO-11-(4-PIPERIDYLIDINE)-5H-BENZO[5,6]CYCLOHEPTA[1,2-B]PYRIDINE ORAL COMPOSITIONS

[75] Inventor: Jim H. Kou, Basking Ridge, N.J.

[73] Assignee: Schering Corporation, Kenilworth, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/348,943

[22] Filed: Jul. 7, 1999

Related U.S. Application Data
[60] Provisional application No. 60/092,291, Jul. 10, 1998.

[51] Int. Cl.$^7$ .................................................. A61K 31/44
[52] U.S. Cl. ............................................................ 514/290
[58] Field of Search ............................................ 514/290

[56] References Cited

U.S. PATENT DOCUMENTS

| | | | |
|---|---|---|---|
| 3,536,809 | 10/1970 | Applezweig | 424/28 |
| 3,598,123 | 8/1971 | Zaffaroni | 128/268 |
| 3,845,770 | 11/1974 | Theeuwes et al. | 128/260 |
| 3,916,899 | 11/1975 | Theeuwes et al. | 128/260 |
| 3,940,485 | 2/1976 | Levinson et al. | 424/250 |
| 4,008,796 | 2/1977 | Aylon | 198/460 |
| 4,282,233 | 8/1981 | Vilani | 424/267 |
| 4,371,516 | 2/1983 | Gregory et al. | 424/22 |
| 4,552,899 | 11/1985 | Sunshine et al. | 514/568 |
| 4,659,716 | 4/1987 | Villani et al. | 514/290 |
| 4,731,447 | 3/1988 | Schumacher et al. | 546/93 |
| 4,777,170 | 10/1988 | Heinrich | 514/226.2 |
| 4,783,465 | 11/1988 | Sunshine et al. | 514/255 |
| 4,804,666 | 2/1989 | Piwinski et al. | 514/278 |
| 4,863,931 | 9/1989 | Schumacher et al. | 514/290 |
| 4,990,535 | 2/1991 | Cho et al. | 514/556 |
| 5,019,591 | 5/1991 | Gardner et al. | 514/461 |
| 5,089,496 | 2/1992 | Piwinski et al. | 514/253 |
| 5,100,675 | 3/1992 | Cho et al. | 424/468 |
| 5,314,697 | 5/1994 | Kwan et al. | 424/480 |
| 5,595,997 | 1/1997 | Aberg et al. | 514/290 |
| 5,731,319 | 3/1998 | Aberg et al. | 514/290 |
| 5,900,421 | 5/1999 | Handley et al. | 514/290 |
| 5,939,426 | 8/1999 | McCullough | 514/290 |

FOREIGN PATENT DOCUMENTS

| | | | |
|---|---|---|---|
| 0288640 A1 | 10/1987 | European Pat. Off. | A61K 31/445 |
| 0396404 A1 | 5/1990 | European Pat. Off. | A61K 31/445 |
| 0396404 B1 | 5/1990 | European Pat. Off. | A61K 31/445 |
| WO 85/03707 | 8/1985 | WIPO | |
| WO 92/00293 | 6/1991 | WIPO | |
| WO 92/11034 | 12/1991 | WIPO | |
| WO 92/00293 | 1/1992 | WIPO | |
| WO 92/20377 | 5/1992 | WIPO | |
| WO 96/16641 | 12/1995 | WIPO | |
| WO 96/20708 | 12/1995 | WIPO | |
| Wo 98/34614 | 8/1998 | WIPO | |

OTHER PUBLICATIONS

Wood, et al., "Mechanisms of antimotion sickness drugs", Aviation, Space, and Environmental Medicine, Sep. 1987, A262–A265.

Wood, "Antimotion sickness and antiemetic drugs", Drugs, 1979, 17:471–479.

Wein, "Pharmacology of incontinence", Urologic Clinics of North America, Aug. 1995, 22(3):557–577.

Van Cauwenberge, "New data on the safety of Loratadine", Drug Invest., 1992, 4(4):283–291.

McCue, "Safety of antihistamines in the treatment of allergic rhinitis in elderly patients", Arch. Fam. Med., 1996, 5:464–468.

Roman, et al., "Loratadine–A review of recent finding in pharmacology phamacokinetics, efficacy, and safety, with a look at its use in combination with pseudoephedrine", Clin. Reviews in Allergy, 1993, 11:89–110.

Simons, "H1–receptor antagonists Comparative tolerability and safety", Drug Safety, 1994, 10(5):350–380.

Temple, et al., "Loratadine, an antihistamine, blocks antigen–and ionophore–induced leukotriene release from human lung in vitro", Prostaglandins, Apr. 1988, 35(4):549–554.

Sunahara, et al., "Pharmacological interventions for motion sickness: Cardiovascular Effects", Aviation, Space and Environmental Medicine, Sep. 1987, A270–A276.

Zhong, et al., "HPLC–Determination of Loratadine and its active metabolite descarboethoxyloratadine inhuman plasma", Pharmazie, 1994, 49(H. 10):736–739.

Yarker, et al., "Oxybutynin,. A review of its pharmacodynamic and phamacokinetic properties, and its therapeutic use in detrusor instability", Drugs and Aging, 1995, 6(3):243–262.

Parkinson, et al., "Evaluation of Loratadine as an inducer of liver microsomal cytochrome P450 in rats and mice", Biochemical Pharmacology, 1992, 43(10):2169–2180.

Van Peer, et al., "Ketoconazole inhibits loratadine metabolism in man", Beerse, Belgium, Abstract 1234, p. 34 (No publication date available).

Peggs, et al, "Antihistamines: The old and the new", American Family Physician, Aug. 1995,52(2):593–600.

(List continued on next page.)

*Primary Examiner*—Raymond Henley, III
*Attorney, Agent, or Firm*—Thomas D. Hoffman

[57] ABSTRACT

Stable pharmaceutical compositions containing 8-chloro-6,11-dihydro-11-(4-piperidylidene)-5H-benzo[5,6]cycloheptic[1,2-b]pyridine("DCL") and a DCL protective amount of a pharmaceutically acceptable basic salt such as calcium dibasic phosphate and an amount of at least one disintegrant, preferably two disintegrates such as microcrystalline cellulose and starch sufficient to provide dissolution of at least about 80% by weight of the pharmaceutical composition in about 45 minutes and suitable for oral administration to treat allergic reactions in mammals such as man are disclosed.

40 Claims, No Drawings

OTHER PUBLICATIONS

Petrin, "Bewegungskrankheit und ihre therapie/Eine Ubersicht (Motion sickness and its treatment)", Schweiz, Rundschau Med., 1974, (PRAXIS) 63:79–81.

Quercia, et al., "Focus on Loratadine: A new second–generation nonsedating H1–receptor antagonist", Hosp. Formul., 1993, 28:137–153.

Resnick, "Urinary incontinence", The Lancet, 1995, 346:94–99.

Massad, et al., "The pharmacokinetics of intravesical and oral oxybutynin chloride", The J. of Urology, Aug. 1992, 148:595–597.

Miadonna, et al., "Inhibitory effect of the H1 antagonist loratadine on histamine release from human basophils", Int. Arch Allergy Immunol., 1994, 105:12–17.

Mirakhur, et al., "Glycopyrrolate: pharamacology and clinical use", Anaesthesia, 1983, 38:1195–1204.

Mitchelson, "Pharmacological agents affecting emesis: A review (Part II)", Drugs, 1992, 43(4):443–463.

Muskat, et al., "The use of scopolamine in the treatment of detrusor instability", The J. of Urology, 1996, 156:1989–1990.

Nelemans, *Side Effects of Drugs Annual 12*, Elsevier Science Publishers B.V., 1988, 144–147.

Kohl, et al., "New pharmacologic approaches to the prevention of space/motion sickness", J. Clin. Pharmacol., 1991, 31:934–946.

Kohl, et al., "Control of nausea and autonomic dysfunction with terfenadine, a peripherally acting antihistamine", Aviation, Space, and Environmental medicine, May 1991, 392–396.

Kubo, et al., "Antimuscarinic effects of antihistamines: Quantitative evaluation by receptor–binding assay", Japan. J. Pharmacol., 1987, 43:277–282.

Lathers, et al., "Pharmacology in space: Part 2. Controlling motion sickness", TiPS, Jun. 1989, 10:243–250.

Levin, et al., "Direct measurement of the anticholinergic activity of a series of pharmacological compounds on the canine and rabbit urinary bladder", The J. of Urology, Aug. 1982, 128:396–398.

Lunde, *Side Effects of Drugs Annual* 14, Elsevier Science Publishers B.V., 1990, 135–143.

Housley, et al., "Histamine and related substances influence neurotransmission in the semicircular canal", Hearing Research, 1988, 35:87–98.

Jankowski, et al., "Effect of terfenadine on nasal provocation", Int. Arch. Allergy Immunol., 1993, 101:311–317.

Kaliner, "Nonsedating antihistamines: Pharmacology, clinical efficacy and adverse effects", American Family Physician, Mar. 1992, 45(3):1337–1342.

Kleine–Tebbe, et al., "Inhibition of IgE–and non–IgE–mediated histamine release from human basophil leukocytes in vitro by a histamine H1–antagonist, desethoxycarbonyl–loratadine", J. Allergy Clin. Immunol., 1994, 93:494–500.

Knowles, "Astemizole and terfenadine–induced cardiovascular effects", The Canadian J. of Hospital Pharmacy, Feb. 1992, 45(1):33–37.

Kohl, et al., "Lack of effects of astemizole on vestibular ocular reflex, motion sickness, and cognitive performance in man", Aviation, Space, and Environmental Medicine, Dec. 1987, 1171–1174.

Dorje, et al., "Antagonist binding profiles of five cloned human muscarinic receptor subtypes", The J. of Pharm. And Experimental Therapeutics, 1991, 256:727–733.

Lunde, *Side Effects of Drugs Annual 12; A worldwide yearly survey of new data and trends,* Elsevier Science Publishers B.V., 1988, 142–143.

Ebert, "Soft elastic gelatin capsules: a unique dosage form", Pharmaceutical Technology, 1977, 44–50.

Gengo, "Dilemma: Antihistamine selection: Use vs. Side effects", U.S. Pharmacist, Nov. 1990, 59–92.

Regula Herzog, et al., *Annual Review of Gerontology and Geriatrics,* 1989, 9:74–119.

Hilbert, et al., "Pharmacokinetics and dose proportionality of loratadine", J. Clin. Pharmacol. 1987, 27:694–698.

Brion, et al., "Evaluation of the antimuscarinic activity of atropine, terfenadine and mequitazine in healthy volunteers", Br. J. clin. Pharmac. 1988, 25:27–32.

Carmeliet, "Voltage–and time–dependent block of the delayed K+current in cardiac myocytes by dofetilide", The J. of Pharm. And Experimental Therapeutics, 1992, 262(2):809–817.

Cheung, et al., "Investigation of anti–motion sickness drugs in the squirrel monkey", J. Clin. Pharmacol, 1992, 32:163–175.

Clissold, et al., "Loratadine a preliminary review of its pharmacodynamic properties and therapeutic efficacy", Drugs, 1989, 37:42–57.

Cooke, "Glycopyrrolate in bladder dysfunction", SA Medical Journal, 1983, 3.

Craft, "Torsade de pointes after astemizole overdose", Br. Medical Journal, 1986, 292:660.

Andersen, et al., "Adverse drug interactions clinically important for the dermatologist", Arch Dermatol, 1995, 131:468–473.

Barnett, et al., *New Perspectives in Histamine Research,* Birkhauser Verlag Basel, pp. 181–196 (1991).

Berge, et al., "Pharmaceutical salts", J. of Pharm. Sciences, 1997, 66(1):1–19.

Berthon, et al., "*In Vitro* inhibition, by loratadine and descarboxyethoxyloratadine, of histamine release from human basophils, and of histamine release and intracellular calcium fluxes in rat basophilic leukemia cells (RBL–2H3)", Biochem. Pharm., 1994 47(5):789–794.

Brandes, et al., "Enhanced cancer growth in mice administered daily human–equivalent doses of some H1–antihistamines: predictive in vitro correlates", J. of the National Cancer Inst., 1994, 86(10):770–775.

Brandes, et al., "Stimulation of malignant growth in rodents by antidepressant drugs at clinically relevant doses", Cancer Research, 1992, 52:3796–3800.

Hartauer, et al., "A comparison of diffuse reflectance FT–IR spectroscopy and DSC in the charaterization of a drug–excipient interaction", Drug Development and Industrial Pharmacy, 1991, 17(4):617–630.

Blaug, et al., "Interaction of dextroamphetamine sulfate with stpay–dried lactose", J. of Pharm. Sciences, 1972, 61(11):1770–1775.

Castello, et al. "Discoloration of tablets containing amines and lactose", J. of Pharm. Sciences, 1962, 51(2):106–108.

Wade, et al., *Handbook of Pharmaceutical Excipients* (2$^{nd}$ edition), American Pharma. Assoc. & the Pharma. Press, Royal Pharma. Society of G. Britain, pp. 257–259 (1994).

Wirth, et al., "Maillard reaction of lactose and fluoxetine hydrochloride, a secondary amine", J. of Pharm. Sciences, 1998, 87(1):31–39.

Babe, et al., The Pharmacological Basis of Therapeutics (9$^{th}$ edition), The McGraw–Hill Co., Inc., pp. 581–599 (1996).

8-CHLORO-6,11-DIHYDRO-11-(4-PIPERIDYLIDINE)-5H-BENZO[5,6]CYCLOHEPTA[1,2-B]PYRIDINE ORAL COMPOSITIONS

CROSS REFERENCE TO RELATED APPLICATIONS:

This application claims priority under 35 U.S.C. 119(e) of provisional application Ser. No.: 60/092,291, filed on Jul. 10, 1998.

BACKGROUND OF THE INVENTION

This invention relates to pharmaceutical compositions containing 8-chloro-6,11-dihydro-11-(4-piperidylidene)-5H-benzo[5,6]-cyclohepta[1,2-b]pyridine (hereinafter "descarbonylethoxyloratadine" or ("DCL") and substantially free of DCL decomposition products, and suitable for oral administration to treat allergic reactions in mammals.

U.S. Pat. No. 4,659,716 discloses descarbonylethoxyloratadine which possesses antihistaminic properties with substantially no sedative properties. This U.S. Patent also discloses methods of making descarbonylethoxyloratadine, pharmaceutical compositions it and methods of using the compositions to treat allergic reactions in mammals.

U.S. Pat. No. 5,595,997 discloses pharmaceutical compositions and methods for treating allergic rhinitis using descarbonylethoxyloratadine. Co-pending, commonly-owned U.S. patent application Ser. No. 08/886,766, filed Jul. 2, 1997 discloses polymorphs of descarbonyl-ethoxyloratadine and pharmaceutical compositions containing them.

We are aware of no prior art that discloses the pharmaceutical compositions of the present invention.

There is a need to produce pharmaceutical compositions suitable for oral administration to mammals and containing descarbonylethoxyloratadine having constant chemical and physical properties in accordance with exacting health registration requirements of the U.S. and international health registration authorities, e.g., the FDA's Good Manufacturing Practices ("GMP") requirements and the International Conference on Harmonization ("ICH") Guidelines.

SUMMARY OF THE INVENTION

We have found that descarbonylethoxyloratadine discolors and decomposes in the presence of excipients disclosed in the prior art. We have discovered that these problems are substantially solved when the use of an acidic excipient is avoided and descarbonylethoxyloratadine is combined with a pharmaceutically acceptable carrier medium comprising a DCL-protective amount of a pharmaceutically acceptable basic salt. Thus, this invention provides a pharmaceutical composition comprising an anti-allergic effective amount of descarbonylethoxyloratadine in a pharmaceutically acceptable carrier medium comprising a DCL-protective amount of a pharmaceutically acceptable basic salt.

The pharmaceutical compositions of the present invention contain less than about 1% of decomposition products such as N-formylDCL initially, as well as when such compositions are stored at 25° C. and about 60% relative humidity for period of at least 24 months.

In a preferred embodiment, this invention provides a pharmaceutical composition comprising an anti-allergic effective amount of descarbonylethoxy-loratadine in a pharmaceutically acceptable carrier medium wherein said composition contains less than about 1% by weight of N-formyl DCL, preferably less than about 0.8% of N-formyl DCL, and more preferably less than about 0.6% of N-formyl DCL.

In another preferred embodiment, this invention provides a pharmaceutical composition for oral administration comprising an anti-allergic effective amount of descarbonylethoxyloratadine in a pharmaceutically acceptable carrier medium comprising a DCL-protective amount of a pharmaceutically acceptable basic salt and an amount of at least one disintegrant sufficient to provide dissolution of at least about 80% by weight of the pharmaceutical composition in about 45 minutes.

This invention also provides a pharmaceutical composition for oral administration comprising an anti-allergic effective amount of descarbonylethoxyloratadine in a pharmaceutically acceptable carrier medium comprising a DCL-protective amount of a calcium dibasic phosphate, and an amount of microcrystalline cellulose and of starch sufficient to provide dissolution of at least about 80% by weight of the pharmaceutical composition in about 45 minutes.

In a preferred embodiment, this invention provides a pharmaceutical composition for oral administration comprising an anti-allergic effective amount of descarbonylethoxyloratadine in a pharmaceutically acceptable carrier medium comprising a DCL-protective amount of a calcium dibasic phosphate, and an amount of microcrystalline cellulose and of starch sufficient to provide dissolution of at least about 80% by weight of the pharmaceutical composition in about 45 minutes, and which contains less than about 1% by weight of N-formyldescarbonyl-ethoxyloratadine.

This invention further provides a preferred pharmaceutical composition for oral administration comprising:

| Ingredient | Amount (weight %) |
|---|---|
| Descarbonylethoxyloratadine | about 0.5–15 |
| Calcium Dibasic Phosphate Dihydrate USP | about 10–90 |
| Microcrystalline Cellulose NF | about 5–60 |
| Corn starch NF | about 1–60 |
| Talc USP | about 0.5–20 |

This invention also provides another preferred pharmaceutical composition for oral administration comprising:

| Ingredient | Amount (weight %) |
|---|---|
| Descarbonylethoxyloratadine | about 0.5–15 |
| Calcium Dibasic Phosphate Dihydrate USP | about 45–60 |
| Microcrystalline Cellulose NF | about 20–40 |
| Corn starch NF | about 5–15 |
| Talc USP | about 1–10 |

This invention also provides another preferred pharmaceutical composition for oral administration comprising:

| Ingredient | Amount (weight %) |
|---|---|
| Descarbonylethoxyloratadine | about 1–10 |
| Calcium Dibasic Phosphate Dihydrate USP | about 50–56 |
| Microcrystalline Cellulose NF | about 25–35 |

-continued

| Ingredient | Amount (weight %) |
|---|---|
| Corn Starch NF | about 10–12 |
| Talc USP | about 2–5 |

The pharmaceutical compositions of the present invention are useful for treating allergic reactions in mammals.

DETAILED DESCRIPTION OF THE INVENTION

During the development of the compositions of the present invention, descarbonylethoxyloratadine was found to discolor when stored at 75% relative humidity ("RH") and a temperature of 40° C., alone or in combination with various excipients, such as those disclosed in U.S. Pat. Nos. 4,657,716 and 5,595,997. We discovered that this color instability in the active ingredient was apparently due to a very minute amount of a degradation product caused by the presence of a wide variety of excipients commonly used in oral formulations—especially a tablet formulation. These excipients found unsuitable include acidic excipients including, but not limited to, stearic acid, povidone, and crospovidone, and other acidic excipients having a pH in water less than 7, preferably in the range of about 3 to 5 as well as other excipients such as lactose, lactose monohydrate, sodium benzoate, and Glyceryl Behenate NF sold under the tradename of Compritol 888 The presence of acidic excipients such as stearic acid in a solid powder formulation blend (similar to that of Example 6) containing DCL, lactose monohydrate, and stearic acid resulted in a large amount (14%) of decomposition of descarbonylethoxyloratadine after one week at 40° C. and 75% RH. When the pharmaceutical compositions of the present invention were subjected to the same stressed conditions for a longer period of time, i.e., 3 months, less than about 1% decomposition of descarbonylethoxyloratadine was found in the pharmaceutical compositions of the present invention. See Examples 1–5, 6 and 10 hereinafter. Preferably, the pharmaceutically acceptable carrier medium used in the pharmaceutical compositions of the present invention should be substantially free, i.e., contain less than about 1% by weight, of acidic excipients.

The major decomposition product of DCL found in the pharmaceutical compositions of the present invention is N-formylDCL. The pharmaceutical compositions of the present invention contain less than about 1% by weight, initially and at periods up to at least 24 months. Preferably, the pharmaceutical compositions of the present invention contain less than about 0.8% by weight, and more preferably they less than about 0.6% by weight of N-formylDCL when such compositions were stored at about 25° C. and about 60% RH for at least 24 months.

The term "pharmaceutically acceptable basic salts" as used herein means a calcium, magnesium or aluminum salt, or mixtures thereof, including, but not limited to carbonates, phosphates, silicates and sulfates of calcium, magnesium and aluminum. Typically suitable pharmaceutically acceptable basic salts include calcium sulfate anhydrous, hydrates of calcium sulfate, such as calcium sulfate dihydrate, magnesium sulfate anhydrous, hydrates of magnesium sulfate, dibasic calcium phosphate, dibasic calcium phosphate anyhdrous, tribasic calcium phosphate, calcium silicate, magnesium silicate, magnesium trisilicate, aluminum silicate, and magnesium aluminum silicate. The use of calcium phosphate salts is preferred. The use of dibasic calcium phosphate hydrates is more preferred The use of dibasic calcium phosphate dihydrate is most preferred.

The DCL-protective amount of the pharmaceutically acceptable basic salt used in the compositions of the present invention is normally about 50% by weight of the total composition. The w/w ratio of the protective amount of the pharmaceutically acceptable basic salt to the anti-allergic amount of DCL is in the range of about 5:1 to about 60:1, preferably about 7:1 to about 11:1, and most preferably about 10:1 to about 11:1.

The term "disintegrant" as used herein means a pharmaceutically acceptable material or combination of such materials that provides a pharmaceutically acceptable dissolution rate for the compositions of the present invention, preferably a dissolution rate for the compositions of the present invention of at least about 80% by weight in about 45 minutes in accordance with the USP paddle dissolution test <711> on page s 1791–1793 of USP 23/NF 18, 1995, UNITED STATES PHARMA-COPEIAL CONVENTION, INC., Rockville Md. 20852. Normally, the dissolution rate is measured in 0.1N HCl at 37° C. The preferred dissolution rate of the compositions of the present invention is at least about 80% by weight in about 30 minutes, and more preferably, the dissolution rate of the compositions of the present invention is at least about 90% by weight in about 30 minutes.

Typically suitable pharmaceutically acceptable disintegrants include microcrystalline cellulose, starch, e.g., pregelatinized starch and corn starch, mannitol, croscarmellose sodium and confectioner's sugar (a mixture of at least 95% by weight sucrose and corn starch that has been ground to a fine powder).The pharmaceutical compositions of the present invention contain at least one, preferably at least two, and most preferably two pharmaceutically acceptable disintegrates in the w/w ratio of about 1:1 to 3:1. In a preferred embodiment of the present invention, the two pharmaceutically acceptable disintegrates are cellulose, and starch, preferably corn starch, in the w/w ratio of about 2:1 to about 3:1.

The w/w ratio of the protective amount of the pharmaceutically acceptable basic salt to the amount of the pharmaceutically acceptable disintegrant(s) is in the range of about 1.1:1 to about 2:1, preferably about 1.2:1 to about 1.75:1, and most preferably about 1.20:1 to about 1.25:1.

Unexpectedly, we discovered that when descarbonylethoxyloratadine was combined with a carrier medium comprising dibasic calcium phosphate, and microcrystalline cellulose-in the absence of prior art excipients such as stearic acid, or lactose—we produced a pharmaceutical composition that was stable to discoloration when stored for 4 weeks in open petri dishes at a temperature of 40° C. and relative humidity of 75%. In a preferred embodiment of the present invention, the carrier medium also contains corn starch and talc. In place of the corn starch one may substitute pregelatinized starch; the talc may be replaced by PEG 8000. The calcium dibasic phosphate may be replaced by calcium sulfate dihydrate, but use of calcium dibasic phosphate is preferred. No significant changes (less than about 1–2% by weight) were observed in the physical appearance, moisture content, chemical assay of descarbonylethoxyloratadine and dissolution rate of the tablet formulations when a preferred embodiment of the present invention of Example 10 was stored in plastic bottles or blister packages for up to 9 months at 25° C./60% RH or at 30° C./60% RH or for up to 6 months at 40° C./75% RH.

The descarbonylethoxyloratadine used in the present invention may be prepared in accordance with Example VI of U.S. Pat. No. 4,659,716. Descarbonylethoxyloratadine exists in two polymorphic forms (form 1 and form 2) which may be prepared in accordance with the Examples 1–3 and procedures of commonly-owned co-pending U.S. patent application Ser. No. 08/886,766 filed Jul. 2, 1997. These two polymorphic forms interconverted during the manufacture of the tablets formulation of the present invention. While either polymorph form may be used, form 1 is preferred.

Pharmaceutical Compositions Pharmaceutical compositions of this invention contain an anti-allergically effective amount of descarbonylethoxyloratadine as the active ingredient, and a pharmaceutically acceptable carrier medium which may include, in addition to specific amounts of calcium dibasic phosphate and microcrystalline cellulose, other inert pharmaceutically acceptable ingredients that may be solids or liquids. Solid form compositions include powders, tablets, dispersible granules, capsules, cachets, and suppositories. The inert pharmaceutically acceptable carrier medium includes one or more substances which may also act as diluents, flavoring agents, solubilizers, lubricants, suspending agents, binders, tablet disintegration agents or encapsulating materials. The solid dosage forms of the pharmaceutical compositions of the present invention are suitable for oral administration and include powders, tablets, dispersible granules, capsules, cachets, buccals, and suppositories. In powders, the carrier medium is a finely divided solid which is in admixture with the finely divided active ingredient. In the tablet, the active ingredient is mixed with carrier medium having the necessary binding properties in suitable proportions and compacted in the shape and size desired. The anti-allergic effective amount of DCL in the pharmaceutical compositions of this invention, e.g., powders and tablets is from about 0.5 to about 15 percent, preferably about 0.5 to 10 weight percent, and more preferably about 1 to 10 weight percent. The term "compositions" is intended to include the formulation of the active compound with encapsulating material as carrier providing a capsule in which the active ingredient (with or without other carriers) is surrounded by carrier medium, which is thus in association with it. Similarly, caches are included.

The anti-allergic effective amount of descarbonylethoxyloratadine for oral administration varies from about 1 to 50 mg/day, preferably about 2.5 to 20 mg/day and more preferably about 5 to 10 mg/day in single or divided doses. The most preferred amount is 5 mg, once a day.

Of course the precise dosage and dosage regimen may be varied depending upon the requirements of the patients (e.g.. his or her sex, age) as well as the severity of the allergic condition being treated. Determination of the proper dosage and dosage regimen for a particular patient will be within the skill of the attending clinician.

Descarbonylethoxyloratadine possess antihistaminic properties. These antihistaminic properties have been demonstrated in standard animal models, such as prevention of histamine—induced lethality in guinea pigs. Antihistaminic activity of polymorph form 1 and form 2 of descarbonylethoxyloratadine has also been demonstrated in a monkey model.

General Experimental

Descarbonylethoxyloratadine may be prepared in accordance with Example VI of U.S. Pat. No. 4,659,716. Calcium dibasic phosphate dihydrate $[Ca(H_2PO_4)_2.2H_2O]$ is available from Rhone Poulenc Rorer, Shelton, Conn. 06484; microcrystalline cellulose is available from FMC Corporation Food & Pharmaceutical Products, Philadelphia, Pa. 19103, corn starch NF is available from National Starch & Chemical Corp., Bridgewater, N.J. 08807 and the talc USP is available from Whittaker, Clark and Daniels, Inc., South Plainfield, N.J.

Method of Manufacture of Pharmaceutical Compositions of the Present Invention in the Form of Tablets The following procedure illustrates the formulation of tablets:

Starch paste preparation

1. Prepare a 10 w/w starch paste by dispersing the paste portion of corn starch into a portion of purified water in a suitable container equipped with an agitator.
2. While mixing, heat the contents of the container to 95° C. and maintain this temperature for 30 minutes.
3. Add an additional amount of purified water to the heated mixture and allow the so-formed starch paste to cool to approximately 50° C.
4. While mixing, add the descarbonylethoxyloratadine to the starch paste.

Granulation

5. To a suitable fluid bed processing bowl, charge the dibasic calcium phosphate dihydrate, a portion of the corn starch and a portion of the microcrystalline cellulose. Place the processing bowl into a fluid bed processor.
6. Fluidize the powder bed and mix for 3 minutes.
7. Begin granulating the powder by pumping the starch paste of step 4 into the fluidized bed at a suitable spray rate (for a 600,000 tablet batch size, the spray rate was 500 mL/min.) and a bed temperature of 22° C.
8. Continue to dry the granulation at 60° C. until the granulation has a final loss on drying of 2% or less.
9. Pass the dried granulation through a suitable sieve or mill.
10. Charge the granulation to a suitable blender and add the requisite amount of the remaining portion of microcrystalline cellulose, corn starch, and talc. Blend for 5 minutes to produce a uniform powder blend.

The resulting blend may be filled into suitable two-piece hard gelatin capsules on a suitable encapsulating machine. The blend may also be compressed to an appropriate size and weight on a suitable tablet machine.

Tableting

1. Compress the final powder blend on a suitable tablet press with a target tablet weight of 100 mg and hardness of 7–9 s.c.u. (Strong-Cobb Units)

The tablets may be film-coated by charging the compressed tablets into suitable coating equipment having a rotating pan and heater. The tablets on the rotating pan are contacted at a temperature of about 30–50° C. with a coating solutions formed by dissolving clear or colored coating materials in purified water. After the tablets are completely coated, a polishing powder may be added to the coated tablets to provide polished coated tablets. Alternatively, the colored coating material may be added as a dry powder in step 5 or 10, preferably step 5 of the Granulation phase of the process. It is preferred that the colored coating material is preferably substantially free, i.e., < about $^1$%, or more preferably completely free of offensive excipients such as lactose.

EXAMPLES 1–5

Follow the above-listed manufacturing procedure using the ingredients listed below and compress the powder blend into tablets.

| Ingredients | 1 mg strength (mg/tab) | 2.5 mg strength (mg/tab) | 5 mg strength (mg/tab) | 7.5 mg strength (mg/tab) | 10 mg strength (mg/tab) |
|---|---|---|---|---|---|
| Descarbonyl-ethoxyloratadine | 1 | 2.5 | 5 | 7.5 | 10 |
| Dibasic calcium phosphate dihydrate USP | 53 | 53 | 53 | 53 | 53 |
| Microcrystallulose NF | 32 | 30.5 | 28 | 25.5 | 23 |
| Corn starch NF | 11 | 11 | 11 | 11 | 11 |
| Talc USP | 3 | 3 | 3 | 3 | 3 |
| Total | 100 | 100 | 100 | 100 | 100 |

EXAMPLES 6–9

The tablet formulations of Examples 6–9 were prepared in accordance with procedure of Examples 1–5.

Example 6

| Ingredients | mg/tablet |
|---|---|
| Descarabonylethoxyloratadine | 10 |
| Lactose monohydrate | 69 |
| Corn starch | 18 |
| Stearic acid | 2 |
| Silicon dioxide | 1 |

Example 7

| Ingredients | mg/tablet |
|---|---|
| Descarabonylethoxyloratadine | 10 |
| Lactose monohydrate | 59 |
| Microcrystalline cellulose | 8 |
| Pregelinized starch | 15 |
| Croscarmellose sodium | 5 |
| Silicon dioxide | 1 |
| Stearic acid | 2 |

Example 8

| Ingredients | mg/tablet |
|---|---|
| Descarabonylethoxyloratadine | 2.5 |
| Dibasic calcium phosphate Dihydrate | 78.5 |
| Corn starch | 18 |
| Magnesium stearate | 1 |

Example 9

| Ingredients | mg/tablet |
|---|---|
| Descarabonylethoxyloratadine | 2.5 |
| Microcrystalline cellulose | 10 |
| Mannitol | 71.5 |
| Pregelinized starch | 15 |
| Magnesium stearate | 1 |

The tablet formulations of Examples 6–9 prepared in accordance with procedure of Examples 1–5 discolored rapidly when they were placed in open petri dishes after less than one week under a temperature of 40° C. and a relative humidity of 75%.

Color stability of Formulated Tablets of Examples 1–5

The color stability of the above mentioned tablets of Examples 1–5 was studied in open petri dishes under a stressed condition of a temperature of 40° C. and 75% relative humidity. After storage in the open petri dishes under this condition for 4 weeks, the tablets of Examples 1–5 were found to be free of discoloration and remained white in color. When descarabonyl-ethoxyloratadine was formulated with other excipients such as lactose and stearic acid and formed into tablets, in accordance with the procedures of Examples 1–5, the tablets of Examples 6–9 discolored rapidly after less than one week under the same storage conditions. A solid powder formulation blend(similar to that of the tablets of Examples 6) containing DCL, lactose monohydrate and stearic acid in the w/w/w/ ratio of 1:7:0.2 also decomposed rapidly after less than one week under the same storage conditions of a temperature of 40° C. and 75% relative humidity; the chemical assay for descarabonylethoxyloratadine in this solid powder formulation was about 86% of the initial amount and the color of the formulation was pink.

Example 10

The procedures of Examples 1–5 were followed except that the formulation of Example 3 was compressed into tablets and filmed coated and polished.

| Ingredients | mg/tablet |
|---|---|
| Descarabonylethoxyloratadine | 5.0 |
| Dibasic calcium phosphate Dihydrate USP | 53.00 |
| Microcrystalline cellulose NF | 28.00 |
| Corn starch NF | 11.00 |
| Talc NF | 3.00 |
| Film coat (blue) | 6.00 |
| Film coat (clear) | 0.6 |
| Polishing Wax[1] | 0.01 |

[1]The polishing wax is a 1:1 w/w mixture of Carnuba wax and white wax.

The stability of Formulated Tablets of Example 10

Chemical assay, physical properties, and photostability of the formulated tablets of Examples 10 were measured on samples placed in high density polyethylene bottles and blister packages.

No significant changes (<1–2%) were observed in the physical appearance, moisture content, chemical assay of descarbonylethoxyloratadine and dissolution rate when the tablets of Example 10 was stored in plastic bottles or blister packages for up to 9 months at 25° C./60% relative humidity ("RH") or at 30° C./60% RH or for up to 6 months at 40°

C./75% RH. A small amount of degradation, e.g., N-formylDCL, was observed in the tablets stored in bottles (about 0.8%) and in blisters( about 1.2%) at 40 C./75% RH for 6 months; only about 0.2–0.3% of the degradation product was observed in any samples of the tablets stored in blisters or bottles for 9 months at 25° C./60% or at 30° C./60% RH. It is expected that the International Conference on Harmonization("ICH") Impurity Guideline for a 5 mg tablet stored for 24 months at 25° C./60% RH or for 12 months at 30° C./60% RH of 1% by weight of the tablet will be met. When the tablets in an open dish were subjected to ICH light conditions for one week at 25° C., the total amount of decomposition products was $0.^{34}\%$ by weight.

Example 11

The procedures of Examples 10 were followed except that the Blue lake was added as a dry powder to step 5 of the Granulation phase and the formulation was thereafter compressed into tablets

| Ingredients | mg/tablet |
| --- | --- |
| Descarabonylethoxyloratadine | 5.0 |
| Dibasic calcium phosphate Dihydrate USP | 53.00 |
| Microcrystalline cellulose NF | 27.72 |
| Corn starch NF | 11.00 |
| Talc NF | 3.00 |
| FD&C Blue #2 Lake | 0.28 |
| Total | 100.00 |

The formulation of Example 11 is expected to have similar chemical assay, and physical properties and photostability to that observed for the formulation of Example 10.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A pharmaceutical composition for oral administration comprising an anti-allergic effective amount of descarbonylethoxy-loratadine in a pharmaceutically acceptable carrier medium comprising a DCL-protective amount of a pharmaceutically acceptable basic salt and at least one pharmaceutically acceptable disintegrant.

2. The pharmaceutical composition of claim 1 wherein the at least one pharmaceutically acceptable disintegrant is in an amount sufficient to provide dissolution of at least 80% by weight of the pharmaceutical composition in about 45 minutes.

3. The pharmaceutical composition of claim 1 wherein the w/w ratio of the DCL-protective amount of the pharmaceutically acceptable basic salt to said disintegrant is in the range of about 1:1 to 2:1.

4. The pharmaceutical composition of claim 1 wherein the pharmaceutically acceptable basic salt is a calcium, magnesium or aluminum salt, or mixtures thereof.

5. The pharmaceutical composition of claim 1 wherein the pharmaceutically acceptable basic salt is a calcium phosphate salt.

6. The pharmaceutical composition of claim 1 wherein the pharmaceutically acceptable carrier medium is substantially free of acidic excipients.

7. A pharmaceutical composition of claim 1 which contains less than about 1% by weight of N-formyldescarbonylethoxyloratadine after storage at about 25° C. and about 60% relative humidity for at least 24 months.

8. The pharmaceutical composition of claim 1 wherein the w/w ratio of the DCL-protective amount of the pharmaceutically acceptable basic salt to the anti-allergic effective amount descarbonylethoxyloratadine is the range of about 5:1 to about 60:1.

9. A pharmaceutical composition for oral administration comprising an anti-allergic effective amount of descarbonylethoxy-loratadine in a pharmaceutically acceptable carrier medium comprising a DCL-protective amount of calcium dibasic phosphate, an amount of microcrystalline cellulose and of starch sufficient to provide dissolution of at least about 80% by weight of the pharmaceutical composition in about 45 minutes.

10. A pharmaceutical composition of claim 9 which contains less than about 1% by weight of N-formyldescarbonylethoxyloratadine after storage at about 25° C. and about 60% relative humidity for at least 24 months.

11. A pharmaceutical composition for oral administration comprising an anti-allergic effective amount of descarbonylethoxy-loratadine in a pharmaceutically acceptable carrier medium comprising a DCL-protective amount of calcium dibasic phosphate, an amount of microcrystalline cellulose and of starch sufficient to provide dissolution of at least 80% by weight of the pharmaceutical composition in about 45 minutes, and containing less than about 1% by weight of N-formyldescarbonyl-ethoxyloratadine after storage at about 25° C. and about 60% relative humidity for at least 24 months.

12. A pharmaceutical composition of claim 9 which comprises:

| Ingredient | Amount (weight %) |
| --- | --- |
| Descarbonylethoxyloratadine | about 0.5–15 |
| Calcium Dibasic Phosphate Dihydrate USP | about 10–90 |
| Microcrystalline Cellulose NF | about 5–60 |
| Corn starch NF | about 1–60 |
| Talc USP | about 0.5–20. |

13. A pharmaceutical composition of claim 9 which comprises:

| Ingredient | Amount (weight %) |
| --- | --- |
| Descarbonylethoxyloratadine | about 0.5–15 |
| Calcium Dibasic Phosphate Dihydrate USP | about 45–60 |
| Microcrystalline Cellulose NF | about 20–40 |
| Corn starch NF | about 5–15 |
| Talc USP | about 1–10. |

14. A pharmaceutical composition of claim 11 wherein the amount of descarbonylethoxyloratadine is in the range of about 1 to about 10 weight percent.

15. A pharmaceutical composition of claim 9 which comprises:

| Ingredient | Amount (weight %) |
| --- | --- |
| Descarbonylethoxyloratadine | about 1–10 |
| Calcium Dibasic Phosphate Dihydrate USP | about 50–56 |
| Microcrystalline Cellulose NF | about 25–35 |
| Corn Starch NF | about 10–12 |
| Talc USP | about 2–5. |

16. The pharmaceutical composition of claim 1 which contains less than about 1% by weight of N-formyldescarbonylethoxyloratadine.

17. A pharmaceutical composition comprising an anti-allergic effective amount of descarbonylethoxyloratadine in a pharmaceutically acceptable carrier medium comprising a DCL-protective amount of a pharmaceutically acceptable basic salt.

18. The pharmaceutical composition of claim 17 wherein said composition further comprises at least one pharmaceutically acceptable disintegrant.

19. The pharmaceutical composition of claim 18 wherein the at least one pharmaceutically acceptable disintegrant is in an amount sufficient to provide dissolution of at least about 80% by weight of the pharmaceutical composition in about 45 minutes.

20. The pharmaceutical composition of claim 19 wherein the w/w ratio of the DCL-protective amount of the pharmaceutically acceptable basic salt to said disintegrant is in the range of about 1:1 to 2:1.

21. The pharmaceutical composition of claim 18 wherein the pharmaceutically acceptable basic salt is a calcium, magnesium or aluminum salt, or mixtures thereof.

22. The pharmaceutical composition of claim 18 wherein the pharmaceutically acceptable basic salt is a calcium phosphate salt.

23. The pharmaceutical composition of claim 18 wherein the pharmaceutically acceptable carrier medium is substantially free of acidic excipients.

24. A pharmaceutical composition of claim 18 which contains less than about 1% by weight of N-formyldescarbonylethoxyloratadine.

25. The pharmaceutical composition of claim 18 wherein the w/w ratio of the DCL-protective amount of the pharmaceutically acceptable basic salt to the anti-allergic effective amount of descarbonylethoxyloratadine is the range of about 5:1 to about 60:1.

26. A pharmaceutical composition comprising an anti-allergic effective amount of descarbonylethoxyloratadine in a pharmaceutically acceptable carrier medium wherein said composition contains less than about 1% by weight of N-formylDCL.

27. The pharmaceutical composition of claim 26 wherein said composition is adapted for oral administration.

28. The pharmaceutical composition of claim 26 wherein said composition has been stored at about 25° C. and about 60% relative humidity for at least 24 months.

29. The pharmaceutical composition of claim 1 wherein the w/w ratio of the DCL-protective amount of tje pharmaceutically acceptable basic salt to said disintegrant is in the range of about 1.5:1 to about 2:1.

30. The pharmaceutical composition of claim 1 wherein the w/w ratio of the DCL-protective amount of the pharmaceutically acceptable basic salt to said disintegrant is in the range of about 1.25:1 to about 1.75:1.

31. The pharmaceutical composition of claim 1 wherein the w/w ratio of the DCL-protective amount of the pharmaceutically acceptable basic salt to the anti-allergic effective amount descarbonylethoxyloratadine is the range of 7:1 to about 11:1.

32. The pharmaceutical composition of claim 1 wherein the w/w ratio of the DCL-protective amount of the pharmaceutically acceptable basic salt to the anti-allergic effective amount descarbonylethoxyloratadine is the range of about 10:1 to about 11:1.

33. The pharmaceutical composition of claim 19 wherein the w/w ratio of the DCL-protective amount of the pharmaceutically acceptable basic salt to said disintegrant is in the range of about 1.5:1; to about 2:1.

34. The pharmaceutical composition of claim 19 wherein the w/w ratio of the DCL-protective amount of the pharmaceutically acceptable basic salt to said disintegrant is in the range of about 1.25:1 to about 1.75:1.

35. The pharmaceutical composition of claim 18 wherein the w/w ratio of the DCL-protective amount of the pharmaceutically acceptable basic salt to the anti-allergic effective amount of descarbonylethoxyloratadine is the range of about 7:1 to about 11:1.

36. The pharmaceutical composition of claim 18 whrein the w/w ratio of the DCL-protective amount of the pharmaceutically acceptable basic salt to the anti-allergic effective amount of descarbonylethoxyloratadine is the range of about 10:1 to about 11:1.

37. A pharmaceutical composition comprising an anti-allergic effective amount of descarbonylethoxyloratadine in a pharmaceutically acceptable carrier medium wherein said composition contains less than about less than about 0.8% of N-formylDCL.

38. A pharmaceutical composition comprising an anti-allergic effective amount of descarbonylethoxyloratadine in a pharmaceutically acceptable carrier medium wherein said composition contains less than about 0.6% of N-formylDCL.

39. A pharmaceutical composition comprising 5 mg of descarbonylethoxyloratadine in a pharmaceutically acceptable carrier medium.

40. The pharmaceutical composition of claim 39 whrein said composition contains less than about 1% by weight of N-formylDCL.

* * * * *